United States Patent
Stähle et al.

[11] 3,950,523
[45] Apr. 13, 1976

[54] PHARMACEUTICAL COMPOSITIONS CONTAINING A 5-OXO-2,3-DIHYDRO-IMIDAZO[1,2-A]-S-TRIAZINE AND METHOD OF USE

[75] Inventors: Helmut Stähle; Herbert Köppe; Werner Kummer, all of Ingelheim am Rhein; Wolfgang Hoefke, Budenheim, all of Germany

[73] Assignee: Boehringer Ingelheim GmbH, Ingelheim am Rhein, Germany

[22] Filed: Feb. 10, 1975

[21] Appl. No.: 548,365

Related U.S. Application Data

[62] Division of Ser. No. 450,289, March 12, 1974, Pat. No. 3,887,552.

[30] Foreign Application Priority Data
Mar. 23, 1973  Germany............................ 2314488

[52] U.S. Cl. .............................................. 424/249
[51] Int. Cl.$^2$......................................... A61K 31/53
[58] Field of Search.................................... 424/249

Primary Examiner—Stanley J. Friedman
Attorney, Agent, or Firm—Hammond & Littell

[57] ABSTRACT

Pharmaceutical compositions containing, as an active ingredient, a compound of the formula

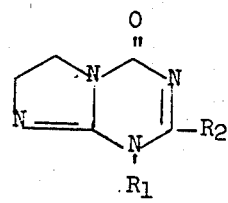

wherein
$R_1$ is phenyl or mono-, di or tri-substituted phenyl, the substituents being each halogen, methyl, methoxy or trifluoromethyl, and
$R_2$ is hydrogen, phenyl or halo-phenyl;
and a method of using the same as antidepressants.

16 Claims, No Drawings

PHARMACEUTICAL COMPOSITIONS CONTAINING A 5-OXO-2,3-DIHYDRO-IMIDAZO[1,2-A]-S-TRIAZINE AND METHOD OF USE

This is a division of copending application Ser. No. 450,289, filed March 12, 1974, now U.S. Pat. No. 3,887,552.

This invention relates to novel pharmaceutical compositions containing a 5-oxo-2,3-dihydro-imidazo[1,2-a]striazine, as well as to methods of using the same as antidepressants.

More particularly, the present invention relates to novel pharmaceutical dosage unit compositions containing, as an active ingredient, a 5-oxo-2,3-dihydro-imidazo[1,2-a]striazine of the formula

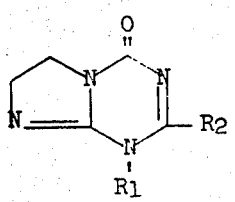
(I)

wherein
$R_1$ is phenyl or mono-, di- or tri-substituted phenyl, the substituents being each selected from the group consisting of halogen, methyl, methoxy and trifluoromethyl, and
$R_2$ is hydrogen, phenyl or halo-phenyl.

The compounds embraced by formula I may be prepared by various methods involving known chemical principles, among which the following have proved to be most convenient and efficient.

METHOD A

By subjecting a 2-phenylamino-2-imidazoline of the formula

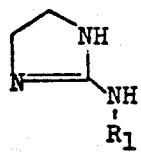
(II)

wherein $R_1$ has the same meanings as in formula I, to a condensation reaction with an N-(halo-methylene or benzylidene)-carbamoyl halide of the formula

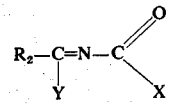
(III)

wherein
$R_2$ has the same meanings as in formula I, and
X and Y, which may be identical to or different from each other, are each halogen, preferably chlorine or bromine.

The condensation may be carried out in a non-polar solvent medium, or also in the absence of a solvent, by heating the reactants to a temperature between 60 and 180°C, preferably 80° and 140°C, advantageously in the presence of an acid-binding agent, such as sodium carbonate, sodium bicarbonate or triethylamine. The intermediates of the formula

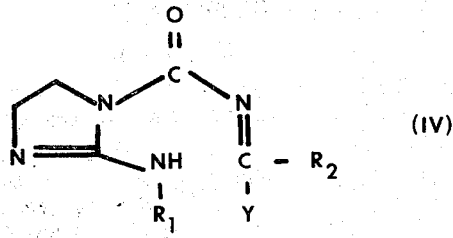
(IV)

where $R_1$, $R_2$ and Y have the meanings previously defined, which are formed by the condensation reaction can normally not be isolated; they very readily and spontaneously cyclize into the desired end products of the formula I.

METHOD B

By reacting a 1-carbamoyl-2-amino-2-imidazoline of the formula

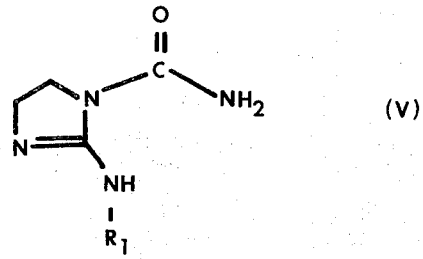
(V)

wherein
$R_1$ has the same meanings as in formula I, with an orthoester of the formula

(VI)

wherein
R is alkyl of 1 to 3 carbon atoms, and
$R_2$ has the same meanings as in formula I. This condensation reaction is preferably performed thermally, in the presence or absence of a solvent medium, at temperatures between 80° and 180°C.

The starting compounds of the formula II are described in Belgian Pat. Nos. 623,305; 687,656; 687,657; and 705,944.

A compound of the formula III may be prepared, for example, by the methods described by R. Neidlein et al in Tetrahedron Letters 28, 2432 (1965) or by S. Yanagida et al in Bull. Chem. Soc. Japan 44, 2182 (1971).

A compound of the formula V may be obtained by reacting a compound of the formula II with a carbamic acid ester.

The orthoesters of the formula VI are well-known compounds.

The following examples illustrate the present invention and will enable others skilled in the art to understand it more completely. It should be understood, however, that the invention is not limited solely to the particular examples given below.

EXAMPLE 1

8-(2',6'-Dichloro-phenyl)-7-(p-chloro-phenyl)-5-oxo-2,3-dihydro-imidazo[1,2-a]s-triazine by method A 2.3 gm (0.01 mol) of 2-[(2',6'-dichloro-phenyl)-amino]-2-imidazoline were dissolved in 50 ml of absolute benzene, 5 ml of triethylamine were added to the solution, the resulting mixture was heated to the boiling point, and, while maintaining it at the boiling point, a solution of 2.4 gm (0.01 mol) of N-(α-chloro-4-chlorobenzylidene)-carbamoyl chloride in 25 ml of absolute benzene was added dropwise over a period of about 15 minutes. The reaction mixture was then boiled for 15 minutes more and was subsequently evaporated to dryness in vacuo. The residue was stirred with dilute hydrochloric acid (to remove impurities which go into solution) and then vacuum-filtered. The filter cake was washed first with water, then with ethanol and finally with ether, blotted on clay, and recrystallized from chloroform, yielding 2.25 gm (52.0% of theory) of the compound of the formula

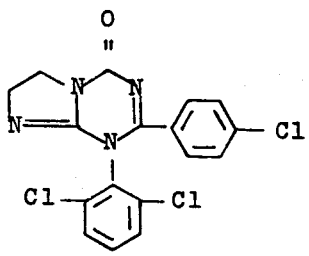

which had a melting point of 320°–322°C. The compound was insoluble in water, dilute hydrochloric acid, ethanol and ether, and soluble in dimethylsulfoxide.

EXAMPLE 2

8-(2',6'-Dichloro-phenyl)-2,3-dihydro-5-oxo-imidazo[1,2-a] s-triazine by method B A mixture consisting of 2.73 gm (0.01 mol) of 1-carbamoyl-2-[(2',6'-dichloro-phenyl)-amino]-2-imidazoline (m.p. 257°–259°C), 5 ml of ethyl orthoformate and 15 ml of hexamethylphosphoric acid triamide (HMPT) was refluxed for two hours. Thereafter, the reaction mixture - which contained three different new compounds, as determined by thin-layer chromatography - was diluted with 200 ml of benzene, and the resulting HMPT/benzene solution was repeatedly washed with water. The organic phase was evaporated in vacuo, the residue was dissolved in dilute hydrochloric acid, and the resulting solution was fractionally extracted at gradually increasing pH-values. Those fractions containing the desired compound, as determined by thin-layer chromatography, were combined and evaporated, yielding 0.15 gm of the compound of the formula

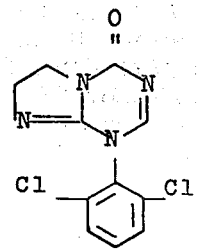

which had a melting point of 155°–157°C.

EXAMPLE 3

Using a procedure analogous to that described in Example 1, 38.6% of theory of 7-(p-chloro-phenyl)-8-(2'-chloro-6'-methyl-phenyl)-5-oxo-2,3-dichloro-imidazo[1,2-a]striazine, m.p. 327°–329°C, of the formula

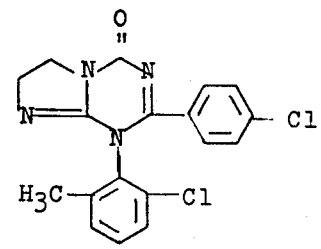

was obtained from 2-[(2'-chloro-6'-methyl-phenyl)-amino]-2-imidazoline and N-(α-chloro-4-chloro-benzylidene)-carbamoyl chloride.

EXAMPLE 4

Using a procedure analogous to that described in Example 1, 26.9% of theory of 7-(p-chloro-phenyl)-8-(2',6'-dichloro-4'-bromo-phenyl)-5-oxo-2,3-dihydro-imidazo[1,2-a]s-triazine, m.p. 285°–288°C, of the formula

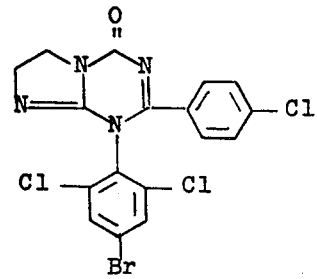

was obtained from 2-[(2',6'-dichloro-4'-bromo-phenyl)-amino]- 2-imidazoline and N-(α-chloro-4-chloro-benzylidene)-carbamoyl chloride.

EXAMPLE 5

Using a procedure analogous to that described in Example 1, 26.9% of theory of 7-(p-chloro-phenyl)-8-(2'-chloro-4'-methyl-phenyl)-5-oxo-2,3-dihydro-imidazo[1,2-a]s-triazine, m.p. 317°–319°C, was obtained from 2-[(2'-chloro-4'-methyl-phenyl)-amino]-2-imidazoline and N-(α-chloro-4-chloro-benzylidene)-carbamoyl chloride.

EXAMPLE 6

Using a procedure analogous to that described in Example 1, 39.0% of theory of 7-phenyl-8-(2',6'-dichlorophenyl)-5-oxo-2,3-dihydro-imidazo[1,2-a]s-triazine, m.p. 239.5°–242.5°C, was obtained from 2-[(2',6'-dichloro-phenyl)amino]-2-imidazoline and N-(α-chloro-benzylidene)-carbamoyl chloride.

EXAMPLE 7

Using a procedure analogous to that described in Example 1, 43.2% of theory of 7-(m-chloro-phenyl)-8-(2',6'-dichloro-phenyl)-5-oxo-2,3-dihydro-imidazo[1,2-a]s-triazine, m.p. 248°–251°C, was obtained from 2-[(2',6'-dichloro-phenyl)-amino]-2-imidazoline and N-(α-chloro-3-chloro-benzylidene)-carbamoyl chloride.

EXAMPLE 8

Using a procedure analogous to that described in Example 1, 32.2% of theory of 7-(m-chloro-phenyl)-8-(2'-chloro-6'-methyl-phenyl)-5-oxo-2,3-dihydro-imidazo[1,2-a]striazine, m.p. 229°–230°C, was obtained from 2-[(2'-chloro-6'-methyl-phenyl)-amino]-2-imidazoline and N-(α-chloro-3-chloro-benzylidene)-carbamoyl chloride.

EXAMPLE 9

Using a procedure analogous to that described in Example 1, 51.0% of theory of 7-(m-chloro-phenyl)-8-(2'-trifluoromethyl-phenyl)-5-oxo-2,3-dihydro-imidazo[1,2-a]s-triazine, m.p. 220°–222°C, of the formula

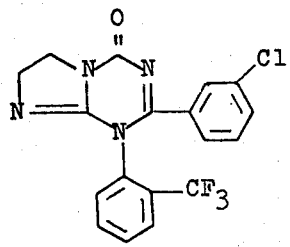

was obtained from 2-[(2'-trifluoromethyl-phenyl)-amino]-2-imidazoline and N-(α-chloro-3-chloro-benzylidene)-carbamoyl chloride.

EXAMPLE 10

Using a procedure analogous to that described in Example 1, 38.2% of theory of 7-(m-chloro-phenyl)-8-(2'-chloro-4'-methyl-phenyl)-5-oxo-2,3-dihydro-imidazo[1,2-a]striazine, m.p. 245°–247°C, was obtained from 2-[(2'-chloro-4'-methyl-phenyl)-amino]-2-imidazoline and N-(α-chloro-3-chloro-benzylidene)-carbamoyl chloride.

EXAMPLE 11

Using a procedure analogous to that described in Example 1, 6.2% of theory of 7-(m-chloro-phenyl)-8-phenyl-5-oxo-2,3-dihydro-imidazo[1,2-a]s-triazine, m.p. 213°–216°C., was obtained from 2-(phenyl-amino)-2-imidazoline and N-(α-chloro-3-chloro-benzylidene)-carbamoyl chloride.

EXAMPLE 12

Using a procedure analogous to that described in Example 1, 28.2% of theory of 7-(m-chloro-phenyl)-8-(2'-chloro-3'-methyl-phenyl)-5-oxo-2,3-dihydro-imidazo[1,2-a]s-triazine, m.p. 248°–249°C., was obtained from 2-[(2'-chloro-3'-methyl-phenyl)-amino]-2-imidazoline and N-(α-chloro-3-chloro-benzylidene)-carbamoyl chloride.

The compounds embraced by formula I above have useful pharmacodynamic properties. More particularly, they exhibit primarily an antidepressant activity in warm-blooded animals, such as rats, rabbits and cats, which, depending upon the particular substitution, is accompanied by less pronounced anti-ulcerogenic, antiphlogistic, diuretic, hypotensive and/or analgesic activities.

For pharmaceutical purposes the compounds of the formula I are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective antidepressant dosage unit of the compounds of the formula I is from 0.0016 to 0.167 mgm/kg body weight.

The following examples illustrate a few pharmaceutical dosage unit compositions comprising a compound of the formula I as an active ingredient and represent the best modes contemplated of putting the invention into practical use. The parts are parts by weight unless otherwise specified.

EXAMPLE 13

Coated pills

The pill core composition is compounded from the following ingredients:

| | | |
|---|---:|---|
| 8-(2',6'-Dichloro-phenyl)-7-(p-chloro-phenyl)-5-oxo-2,3-dihydro-imidazo[1,2-a]s-triazine | 5.0 | parts |
| Lactose | 23.5 | " |
| Corn starch | 20.0 | " |
| Gelatin | 1.0 | " |
| Magnesium stearate | 0.5 | " |
| Total | 50.0 | parts |

Preparation:

The imidazo-s-triazine compound, the lactose and the corn starch are intimately admixed with each other, the mixture is uniformly moistened with an aqueous 10% solution of the gelatin, and the moist mass is granulated by forcing it through a 1 mm-mesh screen. The granulate is then dried at 40°C, again passed through the screen, admixed with the magnesium stearate, and the resulting composition is compressed into 50 mgm-pill cores, which are subsequently coated in conventional fashion with a thin shell consisting essentially of a mixture of sugar, titanium dioxide, talcum and gum arabic, and finally polished with beeswax. Each coated pill contains 5 mgm of the imidazo-s-triazine compound and is an oral dosage unit composition with effective antidepressant action.

EXAMPLE 14

Tablets

The tablet composition is compounded from the following ingredients:

| | | |
|---|---|---|
| 8-(2',6'-Dichloro-phenyl)-5-oxo-2,3-dihydro-imidazo[1,2-a]s-triazine | 2.0 | parts |
| Lactose | 30.0 | " |
| Corn starch | 40.0 | " |
| Colloidal silicic acid | 2.0 | " |
| Magnesium stearate | 1.0 | " |
| Total | 75.0 | parts |

Preparation:

The imidazo-s-triazine compound is intimately admixed with the lactose, the mixture is uniformly moistened with an aqueous starch paste, the moist mass is granulated through a 1 mm-mesh screen, and the granulate is dried. The dry granulate is admixed with the remaining ingredients, and the mixture is compressed into 75 mgm-tablets in a conventional tablet making machine. Each tablet contains 2 mgm of the imidazo-s-triazine compound and is an oral dosage unit composition with effective antidepressant action.

EXAMPLE 15

Suppositories

The suppository composition is compounded from the following ingredients:

| | | |
|---|---|---|
| 8-(2',6'-Dichloro-phenyl)-7-(p-chloro-phenyl)-5-oxo-2,3-dihydro-imidazo[1,2-a]s-triazine | 5.0 | parts |
| Lactose | 195.0 | " |
| Suppository base (e.g. cocoa butter) | 1500.0 | " |
| Total | 1700.0 | parts |

Preparation:

A mixture of the imidazo-s-triazine and the lactose is uniformly blended, with the aid of an immersion homogenizer, into the suppository base which had previously been melted and cooled to 40°C. 1700 mgm-portions of the resulting mixture are poured into cooled suppository molds and allowed to harden therein. Each suppository contains 5 mgm of the imidazo-s-triazine compound and is a rectal dosage unit composition with effective antidepressant action.

Analogous results are obtained when any one of the other imidazo-s-triazines embraced by formula I is substituted for the particular imidazo-s-trizine in Examples 13 through 15. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A pharmaceutical dosage unit composition consisting essentially of an inert pharmaceutical carrier and an effective antidepressant amount of a compound of the formula

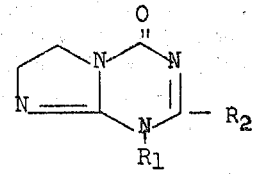

wherein
$R_1$ is phenyl or mono-, di- or tri-substituted phenyl, the substituents being each selected from the group consisting of halogen, methyl, methoxy and trifluoromethyl, and
$R_2$ is hydrogen, phenyl or halo-phenyl.

2. A composition of claim 1, -methylphenyl)- where
$R_1$ is phenyl, methyl-chloro-phenyl, dichloro-phenyl, dichloro-bromo-phenyl or trifluoromethyl-phenyl, and
$R_2$ is hydrogen, phenyl or chloro-phenyl.

3. A composition of claim 2, wherein said compound is 8-(2',6'-dichloro-phenyl)-7-(p-chloro-phenyl)-5-oxo-2,3-dihydro-imidazo[1,2-a]s-triazine.

4. A composition of claim 2, wherein said compound is 8-(2',6'-dichloro-phenyl)-2,3-dihydro-5-oxoimidazo[1,2-a]s-triazine.

5. A composition of claim 2, wherein said compound is 7-(p-chloro-phenyl)-8-(2'-chloro-6'-methyl-phenyl)-5-oxo-2,3-dichloro-imidazo[1,2-a]s-triazine.

6. A composition of claim 2, wherein said compound is 7-(p-chloro-phenyl)-8-(2',6'-dichloro-4'-bromo-phenyl)-5-oxo-2,3-dihydro-imidazo[1,2-a]s-triazine.

7. A composition of claim 2, wherein said compound is 7-(p-chloro-phenyl)-8-(2'-chloro-4'-methylphenyl)-5-oxo-2,3-dihydro-imidazo[1,2-a]s-triazine.

8. A composition of claim 2, wherein said compound is 7-phenyl-8-(2',6'-dichloro-phenyl)-5-oxo-2,3-dihydro-imidazo[1,2-a]s-triazine.

9. A composition of claim 2, wherein said compound is 7-(m-chloro-phenyl)-8-(2',6'-dichloro-phenyl)-5-oxo-2,3-dihydro-imidazo[1,2-a]s-triazine.

10. A composition of claim 2, wherein said compound is 7-(m-chloro-phenyl)-8-(2'-chloro-6'-methyl-phenyl)-5-oxo-2,3-dihydro-imidazo[1,2-a]s-triazine.

11. A composition of claim 2, wherein said compound is 7-(m-chloro-phenyl)-8-(2'-trifluoromethyl-phenyl)-5-oxo-2,3-dihydro-imidazo[1,2-a]s-triazine.

12. A composition of claim 2, wherein said compound is 7-(m-chloro-phenyl)-8-(2'-chloro-4'-methyl-phenyl)-5-oxo-2,3-dihydro-imidazo[1,2-a]s-triazine.

13. A composition of claim 2, wherein said compound is 7-(m-chloro-phenyl)-8-phenyl-5-oxo-2,3-dihydroimidazo[1,2-a]s-triazine.

14. A composition of claim 2, wherein said compound is 7-(m-chloro-phenyl)-8-(2'-chloro-3'-methyl-phenyl)-5-oxo-2,3-dihydro-imidazo[1,2-a]s-triazine.

15. The method of stimulating the mood of a depressed warm-blooded animal, which comprises perorally, parenterally or rectally administering to said animal an effective antidepressant amount of a compound of the formula

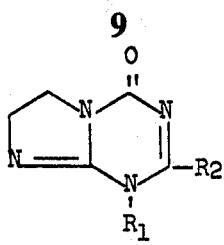

wherein
R₁ is phenyl or mono-, di- or tri-substituted phenyl, the substituents being each selected from the group consisting of halogen, methyl, methoxy and trifluoromethyl, and
R₂ is hydrogen, phenyl or halo-phenyl.

16. The method of claim 15,
where
R₁ is phenyl, methyl-chloro-phenyl, dichloro-phenyl, dichloro-bromo-phenyl or trifluoromethyl-phenyl, and
R₂ is hydrogen, phenyl or chloro-phenyl.

* * * * *